(12) United States Patent
Graham et al.

(10) Patent No.: US 9,339,631 B2
(45) Date of Patent: May 17, 2016

(54) LOCKING MECHANISM FOR A MEDICAL DEVICE

(75) Inventors: Jacob Graham, Watertown, MA (US);
Stephen Derosier, Worcester, MA (US);
Jeffrey Bean, Fitchburg, MA (US); John Golden, Norton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 306 days.

(21) Appl. No.: 12/884,809

(22) Filed: Sep. 17, 2010

(65) Prior Publication Data

US 2011/0077621 A1 Mar. 31, 2011

Related U.S. Application Data

(60) Provisional application No. 61/245,878, filed on Sep. 25, 2009.

(51) Int. Cl.
| | | |
|---|---|---|
| *A61M 25/01* | (2006.01) | |
| *A61M 25/00* | (2006.01) | |
| *A61M 25/06* | (2006.01) | |
| *A61M 25/09* | (2006.01) | |

(52) U.S. Cl.
CPC ........... *A61M 25/01* (2013.01); *A61M 25/0097* (2013.01); *A61M 25/0105* (2013.01); *A61M 25/0136* (2013.01); *A61M 25/0147* (2013.01); *A61M 2025/0681* (2013.01); *A61M 2025/09125* (2013.01)

(58) Field of Classification Search
CPC ............ A61M 37/00; A61M 25/0147; A61M 25/0122; A61M 25/0113; A61M 25/0105; A61M 25/0172; A61M 25/0169; A61M 25/0905; A61M 25/09041; A61M 2025/0163; A61M 25/0152; A61M 25/04

USPC .......... 604/95.04, 280, 510, 528, 95; 607/122
See application file for complete search history.

(56) References Cited

U.S. PATENT DOCUMENTS

| | | |
|---|---|---|
| 2,212,334 A | 8/1940 | Wallerich |
| 2,393,003 A | 1/1946 | Smith |
| 3,100,490 A | 8/1963 | Desautels |

(Continued)

FOREIGN PATENT DOCUMENTS

| | | |
|---|---|---|
| CA | 1112119 A | 11/1981 |
| DE | 3345612 A1 | 6/1985 |

(Continued)

OTHER PUBLICATIONS

Collins English Dictionary: coupled. Accessed online, Dec. 16, 2013.*

*Primary Examiner* — Kami A Bosworth
*Assistant Examiner* — Matthew A Engel
(74) *Attorney, Agent, or Firm* — Kacvinsky Daisak Bluni PLLC

(57) ABSTRACT

A locking mechanism for a medical device to selective lock a first elongate member from longitudinal movement relative to a second elongate member of the medical device. The locking mechanism includes a flexible tubular member disposed in a bore of a handle assembly of the medical device, and an actuator, such as a cam member having a cam or eccentric surface. Pivotable movement of the actuator from a first position to a second position compresses or deforms the flexible tubular member against the first elongate member to lock the first elongate member from longitudinal movement relative to the handle assembly.

14 Claims, 12 Drawing Sheets

(56) References Cited

U.S. PATENT DOCUMENTS

| | | | |
|---|---|---|---|
| 3,332,424 A | 7/1967 | Minteer | |
| 3,421,509 A | 1/1969 | Fiore | |
| 3,500,820 A * | 3/1970 | Torsten | 600/434 |
| 3,592,197 A | 7/1971 | Cohen | |
| 3,783,453 A | 1/1974 | Bolie | |
| 3,908,635 A | 9/1975 | Viek | |
| 3,938,529 A | 2/1976 | Gibbons | |
| 3,995,642 A | 12/1976 | Adair | |
| 4,212,304 A | 7/1980 | Finney | |
| 4,225,979 A | 10/1980 | Rey et al. | |
| 4,242,304 A | 12/1980 | Ryder | |
| 4,248,214 A | 2/1981 | Hannah et al. | |
| 4,307,723 A | 12/1981 | Finney | |
| 4,334,327 A | 6/1982 | Lyman et al. | |
| 4,382,445 A | 5/1983 | Sommers | |
| 4,417,886 A * | 11/1983 | Frankhouser et al. | 604/510 |
| 4,434,797 A | 3/1984 | Silander | |
| 4,474,569 A | 10/1984 | Newkirk | |
| 4,484,585 A | 11/1984 | Baier | |
| 4,500,313 A | 2/1985 | Young | |
| 4,531,933 A | 7/1985 | Norton et al. | |
| 4,545,373 A | 10/1985 | Christoudias | |
| 4,568,338 A | 2/1986 | Todd | |
| 4,592,341 A | 6/1986 | Omagari et al. | |
| 4,610,657 A | 9/1986 | Densow | |
| 4,643,716 A | 2/1987 | Drach | |
| 4,645,493 A | 2/1987 | Ferrando et al. | |
| 4,671,795 A | 6/1987 | Mulchin | |
| 4,684,369 A | 8/1987 | Wildemeersch | |
| 4,698,057 A * | 10/1987 | Joishy | 604/176 |
| 4,699,611 A | 10/1987 | Bowden | |
| 4,713,049 A | 12/1987 | Carter | |
| 4,738,667 A | 4/1988 | Galloway | |
| 4,747,833 A | 5/1988 | Kousai et al. | |
| 4,755,175 A | 7/1988 | Nilsson | |
| 4,762,128 A | 8/1988 | Rosenbluth | |
| 4,783,454 A | 11/1988 | Liu | |
| 4,784,651 A | 11/1988 | Hickey | |
| 4,787,884 A | 11/1988 | Goldberg | |
| 4,790,809 A | 12/1988 | Kuntz | |
| 4,790,810 A | 12/1988 | Pugh, Jr. et al. | |
| 4,813,925 A | 3/1989 | Anderson, Jr. et al. | |
| 4,820,262 A | 4/1989 | Finney | |
| 4,822,333 A | 4/1989 | Lavarenne | |
| 4,824,435 A | 4/1989 | Giesy et al. | |
| 4,832,055 A | 5/1989 | Palestrant | |
| 4,869,719 A * | 9/1989 | Hogan | 604/174 |
| 4,874,360 A | 10/1989 | Goldberg et al. | |
| 4,874,371 A * | 10/1989 | Comben et al. | 604/95.01 |
| 4,886,065 A | 12/1989 | Collins, Jr. | |
| 4,913,141 A | 4/1990 | Hillstead | |
| 4,913,683 A | 4/1990 | Gregory | |
| 4,931,037 A | 6/1990 | Wetterman | |
| 4,950,228 A | 8/1990 | Knapp, Jr. et al. | |
| 4,955,858 A | 9/1990 | Drews | |
| 4,957,479 A | 9/1990 | Roemer | |
| 4,963,129 A | 10/1990 | Rusch | |
| 4,973,301 A | 11/1990 | Nissenkorn | |
| 4,990,133 A | 2/1991 | Solazzo | |
| 4,994,066 A | 2/1991 | Voss | |
| 5,019,085 A | 5/1991 | Hillstead | |
| 5,019,102 A | 5/1991 | Hoene | |
| 5,052,998 A | 10/1991 | Zimmon | |
| 5,098,374 A | 3/1992 | Othel-Jacobsen et al. | |
| 5,116,309 A | 5/1992 | Coll | |
| 5,141,502 A | 8/1992 | Macaluso, Jr. | |
| 5,147,370 A | 9/1992 | McNamara et al. | |
| 5,152,749 A | 10/1992 | Giesy et al. | |
| 5,160,341 A | 11/1992 | Brenneman et al. | |
| 5,234,437 A | 8/1993 | Sepetka | |
| 5,250,071 A | 10/1993 | Palermo | |
| 5,261,916 A | 11/1993 | Engelson | |
| 5,267,958 A | 12/1993 | Buchbinder et al. | |
| 5,282,784 A | 2/1994 | Willard | |
| 5,295,954 A | 3/1994 | Sachse | |
| 5,304,195 A | 4/1994 | Twyford, Jr. et al. | |
| 5,304,198 A | 4/1994 | Samson | |
| 5,320,604 A | 6/1994 | Walker et al. | |
| 5,322,501 A | 6/1994 | Mahmud-Durrani | |
| 5,324,259 A | 6/1994 | Taylor et al. | |
| 5,334,185 A | 8/1994 | Giesy et al. | |
| 5,342,299 A * | 8/1994 | Snoke et al. | 604/95.04 |
| 5,346,467 A | 9/1994 | Coll | |
| 5,347,989 A * | 9/1994 | Monroe et al. | 600/131 |
| 5,348,537 A | 9/1994 | Wiesner et al. | |
| 5,352,237 A * | 10/1994 | Rodak et al. | 606/206 |
| 5,354,263 A | 10/1994 | Coll | |
| 5,358,478 A * | 10/1994 | Thompson et al. | 604/95.04 |
| 5,364,340 A | 11/1994 | Coll | |
| 5,364,354 A | 11/1994 | Walker et al. | |
| 5,364,376 A | 11/1994 | Horzewski et al. | |
| 5,372,600 A | 12/1994 | Beyar et al. | |
| 5,391,155 A | 2/1995 | Sachse | |
| 5,399,165 A * | 3/1995 | Paul, Jr. | 604/95.04 |
| 5,401,257 A | 3/1995 | Chevalier, Jr. et al. | |
| 5,405,378 A | 4/1995 | Strecker | |
| 5,407,435 A | 4/1995 | Sachse | |
| 5,409,468 A | 4/1995 | Sachse | |
| 5,454,788 A | 10/1995 | Walker et al. | |
| 5,458,615 A | 10/1995 | Klemm et al. | |
| 5,462,527 A * | 10/1995 | Stevens-Wright et al. | 604/528 |
| 5,476,505 A | 12/1995 | Limon | |
| 5,480,434 A | 1/1996 | Eckstein et al. | |
| 5,484,409 A | 1/1996 | Atkinson et al. | |
| 5,496,344 A | 3/1996 | Kanesaka et al. | |
| 5,531,686 A * | 7/1996 | Lundquist et al. | 604/95.04 |
| 5,540,236 A | 7/1996 | Ginn | |
| 5,578,009 A | 11/1996 | Kraus et al. | |
| 5,599,291 A | 2/1997 | Balbierz et al. | |
| 5,611,777 A * | 3/1997 | Bowden et al. | 604/95.01 |
| 5,639,274 A | 6/1997 | Fischell et al. | |
| 5,645,533 A | 7/1997 | Blaeser et al. | |
| 5,653,748 A | 8/1997 | Strecker | |
| 5,669,880 A | 9/1997 | Solar | |
| 5,673,841 A * | 10/1997 | Schulze et al. | 227/175.1 |
| 5,676,654 A | 10/1997 | Ellis et al. | |
| 5,681,274 A | 10/1997 | Perkins et al. | |
| 5,690,642 A | 11/1997 | Osborne et al. | |
| 5,693,015 A | 12/1997 | Walker et al. | |
| 5,693,083 A * | 12/1997 | Baker et al. | 623/1.11 |
| 5,776,099 A | 7/1998 | Tremulis | |
| 5,843,002 A * | 12/1998 | Pecor et al. | 600/585 |
| 5,848,986 A * | 12/1998 | Lundquist et al. | 604/22 |
| 5,861,024 A | 1/1999 | Rashidi | 607/122 |
| 5,876,373 A * | 3/1999 | Giba et al. | 604/95.04 |
| 5,904,667 A * | 5/1999 | Falwell | 604/95.01 |
| 5,921,952 A | 7/1999 | Desmond, III et al. | |
| 5,921,971 A | 7/1999 | Agro et al. | |
| 5,987,344 A * | 11/1999 | West | 600/373 |
| 6,033,378 A * | 3/2000 | Lundquist et al. | 604/95.01 |
| 6,095,990 A | 8/2000 | Parodi | |
| 6,159,177 A * | 12/2000 | Amos et al. | 604/95.04 |
| 6,159,195 A | 12/2000 | Ha et al. | |
| 6,235,050 B1 * | 5/2001 | Quiachon et al. | 623/1.11 |
| 6,248,100 B1 | 6/2001 | de Toledo et al. | |
| 6,264,624 B1 | 7/2001 | Desmond, III et al. | |
| 6,394,976 B1 * | 5/2002 | Winston et al. | 604/95.04 |
| 6,423,059 B1 * | 7/2002 | Hanson et al. | 606/41 |
| 6,454,740 B1 * | 9/2002 | Mody | 604/95.04 |
| 6,511,471 B2 * | 1/2003 | Rosenman et al. | 604/528 |
| 6,562,024 B2 | 5/2003 | Alvarez de Toledo et al. | |
| 6,652,506 B2 * | 11/2003 | Bowe et al. | 604/523 |
| 6,663,588 B2 * | 12/2003 | DuBois et al. | 604/95.04 |
| 6,699,183 B1 * | 3/2004 | Wimmer | 600/147 |
| 6,752,800 B1 * | 6/2004 | Winston et al. | 604/528 |
| 7,004,957 B1 * | 2/2006 | Dampney et al. | 606/211 |
| 7,087,038 B2 | 8/2006 | Lee | |
| 7,144,371 B2 | 12/2006 | Edwardsen et al. | 600/459 |
| 7,172,572 B2 * | 2/2007 | Diamond et al. | 604/32 |
| 7,217,256 B2 * | 5/2007 | Di Palma | 604/104 |
| 7,326,224 B2 | 2/2008 | Houde et al. | |
| 7,377,906 B2 * | 5/2008 | Selkee | 604/95.04 |
| 7,442,198 B2 * | 10/2008 | Gellman et al. | 606/144 |
| 7,465,288 B2 * | 12/2008 | Dudney et al. | 604/95.04 |

(56) References Cited

U.S. PATENT DOCUMENTS

| | | | |
|---|---|---|---|
| 7,497,853 B2 * | 3/2009 | Fischer et al. | 604/528 |
| 7,550,002 B2 | 6/2009 | Goto et al. | |
| 7,591,783 B2 * | 9/2009 | Boulais et al. | 600/142 |
| 7,591,784 B2 * | 9/2009 | Butler | 600/146 |
| 7,591,813 B2 * | 9/2009 | Levine et al. | 604/528 |
| 7,615,067 B2 * | 11/2009 | Lee et al. | 606/205 |
| 7,651,519 B2 * | 1/2010 | Dittman | 623/1.11 |
| 7,678,074 B2 * | 3/2010 | Fischer et al. | 604/95.04 |
| 7,740,608 B2 * | 6/2010 | Lampropoulos et al. | 604/95.05 |
| 7,803,130 B2 * | 9/2010 | Ryan et al. | 604/95.04 |
| 7,824,367 B2 * | 11/2010 | Accisano et al. | 604/95.04 |
| 7,879,080 B2 | 2/2011 | Sato | |
| 7,976,530 B2 * | 7/2011 | Johnson et al. | 604/524 |
| 8,048,025 B2 * | 11/2011 | Barenboym et al. | 604/95.04 |
| 8,177,773 B2 * | 5/2012 | Ovcharchyn et al. | 604/540 |
| 2003/0050598 A1 * | 3/2003 | Hayzelden | 604/95.04 |
| 2004/0039373 A1 | 2/2004 | Harding et al. | |
| 2004/0193239 A1 * | 9/2004 | Falwell et al. | 607/122 |
| 2005/0080476 A1 * | 4/2005 | Gunderson et al. | 623/1.11 |
| 2005/0251167 A1 * | 11/2005 | Voegele et al. | 606/153 |
| 2005/0256562 A1 * | 11/2005 | Clerc et al. | 623/1.11 |
| 2006/0212009 A1 | 9/2006 | Accisano, III et al. | |
| 2006/0252993 A1 * | 11/2006 | Freed et al. | 600/146 |
| 2006/0264819 A1 * | 11/2006 | Fischer et al. | 604/95.04 |
| 2007/0156116 A1 * | 7/2007 | Gonzalez | 604/528 |
| 2007/0203474 A1 * | 8/2007 | Ryan et al. | 604/528 |
| 2007/0260225 A1 * | 11/2007 | Sakakine et al. | 604/528 |
| 2007/0293929 A1 | 12/2007 | Aoba et al. | |
| 2009/0088603 A1 * | 4/2009 | Messerly et al. | 600/146 |
| 2009/0143849 A1 | 6/2009 | Ozawa et al. | |
| 2009/0287188 A1 * | 11/2009 | Golden et al. | 604/528 |
| 2009/0312829 A1 | 12/2009 | Aoba et al. | |
| 2010/0004633 A1 * | 1/2010 | Rothe et al. | 604/528 |
| 2010/0087811 A1 * | 4/2010 | Herrin et al. | 606/40 |
| 2010/0191193 A1 | 7/2010 | Pajunk et al. | |
| 2010/0234809 A1 * | 9/2010 | Kenley et al. | 604/180 |
| 2010/0324538 A1 * | 12/2010 | Van Orden | 604/528 |
| 2011/0077621 A1 * | 3/2011 | Graham et al. | 604/528 |
| 2011/0238040 A1 * | 9/2011 | Johnson et al. | 604/524 |
| 2011/0313404 A1 * | 12/2011 | Amos et al. | 604/544 |
| 2011/0319904 A1 * | 12/2011 | Hollett et al. | 606/108 |

FOREIGN PATENT DOCUMENTS

| | | |
|---|---|---|
| DE | 3919740 A1 | 12/1990 |
| DE | 10 2007 029 229 | 12/2008 |
| GB | 2 018 600 A | 10/1979 |
| WO | WO 93/00126 A1 | 1/1993 |
| WO | WO 99/08740 | 2/1999 |

* cited by examiner

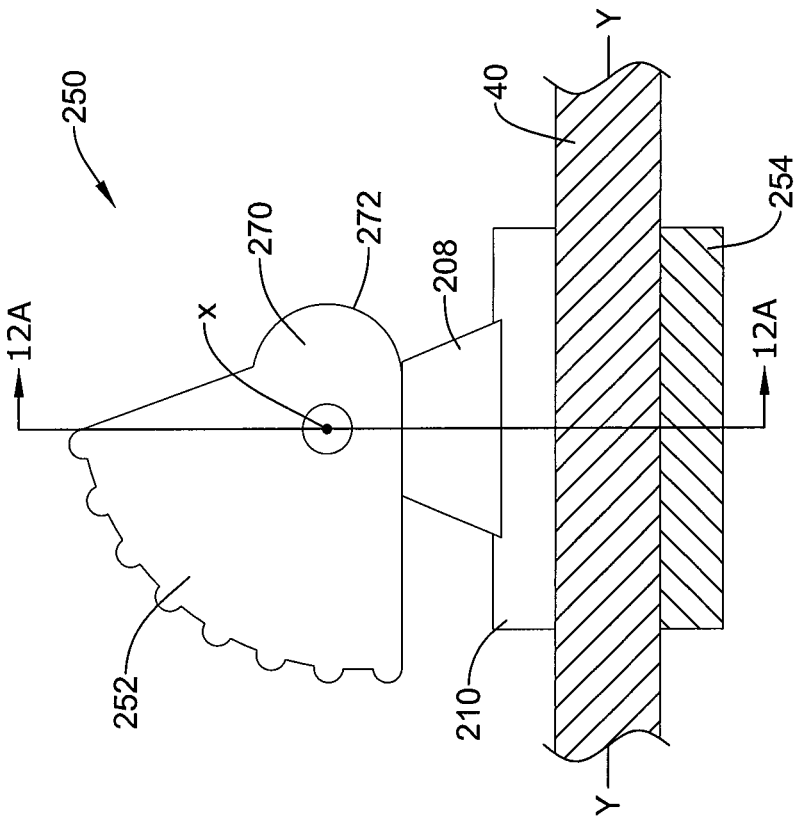
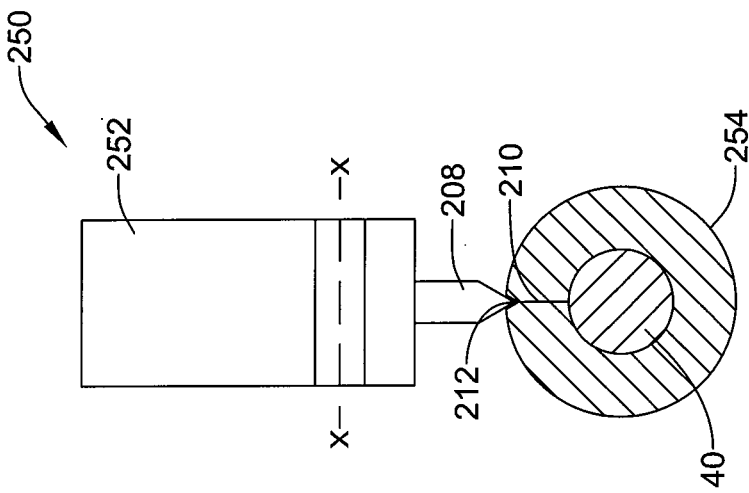
Figure 12
Figure 12A

LOCKING MECHANISM FOR A MEDICAL DEVICE

CROSS REFERENCE TO RELATED APPLICATIONS

This application claims the benefit of U.S. Provisional Application Ser. No. 61/245,878, filed Sep. 25, 2009, the disclosure of which is incorporated herein by reference.

TECHNICAL FIELD

The disclosure is directed to a locking mechanism for a medical device. More particularly, the disclosure is directed to a locking mechanism for selectively locking a first elongate member from longitudinal movement relative to a second elongate member of the medical device.

BACKGROUND

Medical devices, such as catheters, are widely used in various medical procedures to access remote anatomical locations and/or deploy therapeutic devices. During some medical procedures, it may be desirable to selectively lock a first elongate member of the medical device from longitudinal movement relative to a second elongate member of the medical device during a portion of the medical procedure. During another portion of the medical procedure, however, it may be desirable to allow the first elongate member to move longitudinally relative to the second elongate member.

Therefore, it may be desirable to provide a handle assembly of a medical device which includes a locking mechanism which may be actuatable to selectively lock a first elongate member of the medical device from longitudinal movement relative to a second elongate member of the medical device. Selectively locking the first elongate member relative to the second elongate member may prevent inadvertent relative movement between the first and second elongate members during portions of the medical procedure.

SUMMARY

The disclosure is directed to several alternative designs and configurations of medical device structures and assemblies including locking mechanisms.

Accordingly, one illustrative embodiment is a medical device assembly including an elongate tubular member, a handle assembly including a locking mechanism and an elongate member. The handle assembly is coupled to the proximal end of the elongate tubular member. The handle assembly includes a housing having a bore extending therethrough. The bore of the housing includes a first portion having a first diameter and a second portion having a second diameter greater than the first diameter. The locking mechanism includes a flexible member, such as a flexible tubular member, positioned in the second portion of the bore of the housing of the handle assembly and an actuator pivotably attached to the housing of the handle assembly about a pivot axis. The actuator is pivotable between a first position and a second position. The elongate member is selectively longitudinally movable with respect to the housing of the handle assembly. With the actuator in the first position, the elongate member is longitudinally movable along the flexible member, and with the actuator in the second position, longitudinal movement of the elongate member is restrained by the flexible member. The flexible member may not be deformed against the elongate member in the first position, but may be deformed against the elongate member in the second position. In instances in which the flexible member is a tubular member, the lumen of the flexible member may have a diameter which is substantially equal to the first diameter of the first portion of the bore of the housing.

Another embodiment is a medical catheter assembly including an outer tubular member and an inner tubular member disposed in the lumen of the outer tubular member and extending distally therefrom. The medical catheter assembly also includes a handle assembly coupled to the proximal end of the outer tubular member. The handle assembly includes a housing having a proximal end and a distal end, wherein the housing includes a bore extending therethrough. An elongate member is coupled to the inner tubular member and extends proximally therefrom through the lumen of the outer tubular member into the bore of the housing. The handle assembly includes a locking mechanism including an actuator actuatable between a first position and a second position, and a flexible member positioned in the bore of the housing with the elongate member extending along the flexible member. The flexible member is configured to frictionally engage the elongate member. In the first position the elongate member and the inner tubular member are longitudinally movable relative to the outer tubular member and the handle assembly, and in the second position the actuator forces the flexible member against the elongate member to restrain longitudinal movement of the elongate member relative to the handle assembly. In the first position, there may be a first coefficient of friction between a surface of the flexible member and an outer surface of the elongate member, and in the second position, there may be a second coefficient of friction between the surface of the flexible member and the outer surface of the elongate member. The second coefficient of friction being greater than the first coefficient of friction.

Yet another embodiment is a method of selectively locking an elongate member of a medical device with respect to a handle assembly of the medical device. The method includes providing a handle assembly including a housing having a bore extending through the housing. The bore of the housing includes a first portion having a first diameter and a second portion having a second diameter greater than the first diameter. A flexible member is positioned in the second portion of the bore of the housing. An actuator is movably attached to the housing between a first position and a second position. An elongate member is positioned along the flexible member such that the elongate member is longitudinally movable with respect to the housing of the handle assembly with the actuator in the first position. The actuator is actuated to the second position, wherein in the second position the flexible member is compressed against the elongate member to restrain longitudinal movement of the elongate member with respect to the housing of the handle assembly.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which:

FIG. 12 is a cross-sectional view of the locking assembly of FIG. 11 in a second, locked position; and FIG. 12A is a cross-sectional view of the locking assembly of FIG. 12 taken along line 12A-12A.

Figure 1:
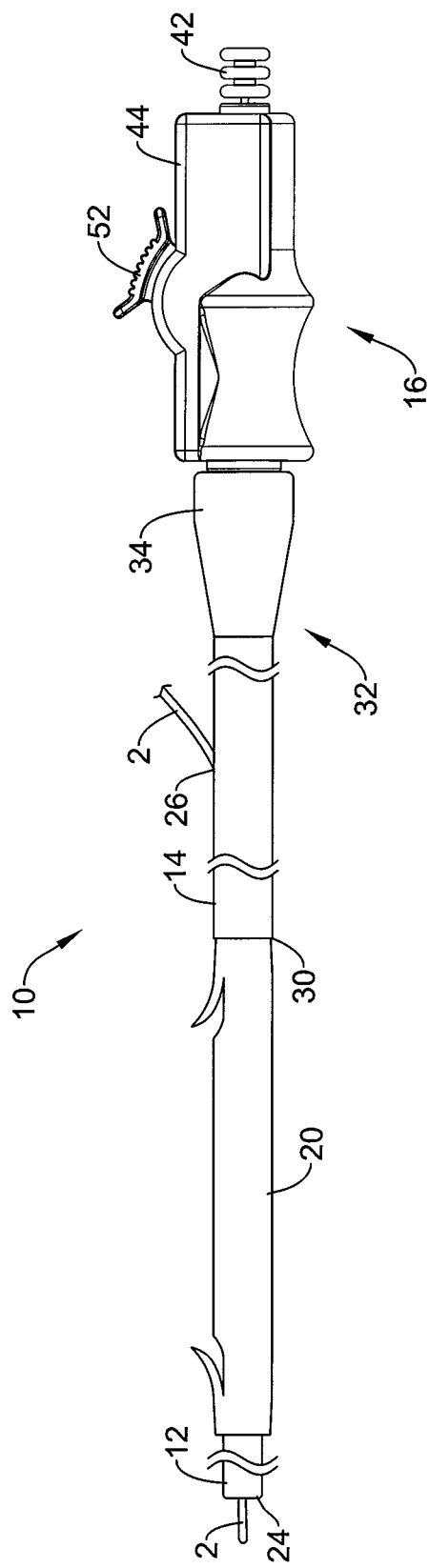
FIG. 1 is a plan view of an exemplary drainage catheter delivery system including a handle assembly having a locking mechanism.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Figure 2:
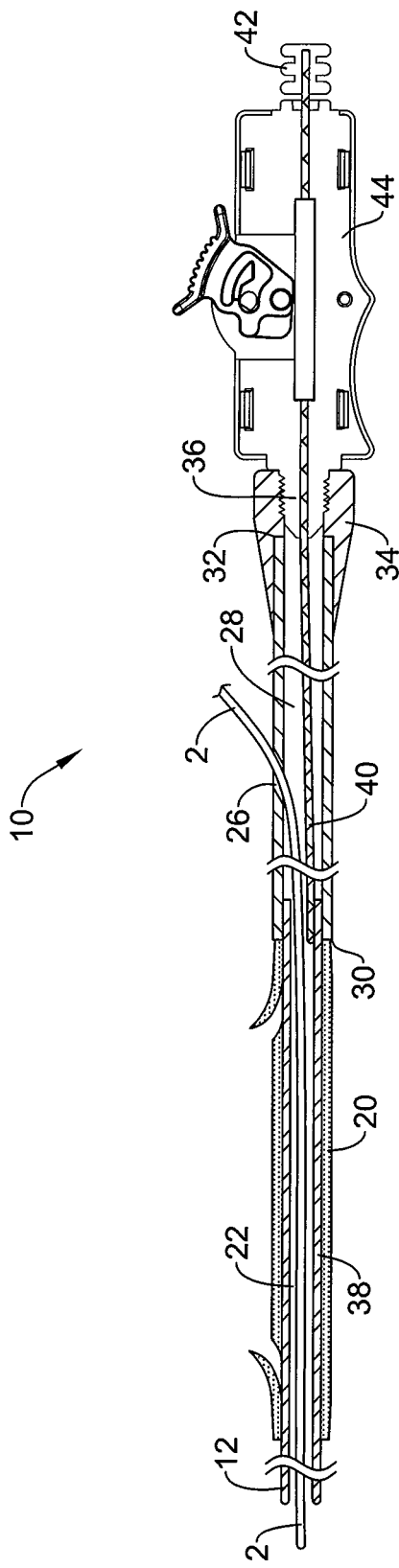
FIG. 2 is a longitudinal cross-sectional view of the drainage catheter delivery system of FIG. 1.

Referring now to FIGS. 1 and 2, there is shown an exemplary medical device illustrated as a drainage catheter delivery system 10 for delivering a drainage catheter or stent 20 to an anatomical location, such as in a lumen of the biliary tree or a ureter. The drainage catheter 20 may be used to bypass or drain an obstructed lumen and can be configured for long-term positioning within the lumen. It should be understood that the terms "drainage catheter" and "stent" can be used interchangeably with reference to these applications.

The drainage catheter delivery system 10 is designed for use with a conventional guidewire 2 and may include a drainage catheter 20, a guide catheter 12, a push catheter 14, and a handle assembly 16. The guidewire 2 may extend into a lumen 22 of the guide catheter 12 through a distal guidewire port 24 and out a guidewire port 26 in a sidewall of the push catheter 14, providing the drainage catheter delivery system 10 with single-operator-exchange (SOE) capabilities.

The guide catheter 12 is slidably disposed in the lumen 28 of the push catheter 14 and extends distally from the distal end of the push catheter 14. The drainage catheter 20 is positioned on a distal portion of the guide catheter 12 located distal of the push catheter 14 and may abut the distal end 30 of the push catheter 14. The drainage catheter delivery system 10 may include a means for releasably connecting the push catheter 14 to the drainage catheter 20. When the drainage catheter 20 has been properly placed, the drainage catheter 20 may be disconnected from the push catheter 14 such that the drainage catheter 20 remains in the lumen when the push catheter 14 is withdrawn. For example, the drainage catheter 20 may be disconnected from the push catheter 14 by withdrawing the guide catheter 12 proximally relative to the drainage catheter 20 and the push catheter 14. Some exemplary drainage catheter delivery systems including means for releasably connecting the push catheter 14 to the drainage catheter 20 are disclosed in U.S. Pat. Nos. 5,921,952 and 6,562,024, the disclosures of which are incorporated herein by reference. For example, a suture (not shown) attached to the push catheter 14, may be threaded around a portion of the drainage catheter 20 and the guide catheter 12. As the guide catheter 12 is moved longitudinally in a proximal direction relative to the drainage catheter 20 and the push catheter 14, the suture may be freed from the guide catheter 12 and the drainage catheter 20, releasing the drainage catheter 20.

The proximal end 32 of the push catheter 14 may be attached to the handle assembly 16. For example, the proximal end 32 may include a female luer lock connector 34 threadably coupled to a threaded male connector 36 of the handle assembly 16. It is understood, however, that the push catheter 14 may be attached to the handle assembly 16 and extend distally therefrom by other means, such as adhesive bonding, welding, friction fit, interlocking fit, molding such as overmolding, or other suitable means.

The guide catheter 12 may include a distal tubular portion 38 and a proximal elongate member 40 connected to the distal tubular portion 38. The elongate member 40, as shown in FIG. 2, may be an elongate wire, such as a pull wire, fixed to the distal tubular portion 38, or the elongate member 40 may be a tubular member in some embodiments. The elongate member 40 may extend through the lumen 28 of the push catheter 14 to the handle assembly 16. In some embodiments, the elongate member 40 may extend through the handle assembly 16 to a location proximal of the handle assembly 16. The proximal end of the elongate member 40 may terminate at a knob 42 which may be grasped by an operator to manipulate the guide catheter 12.

Figure 3:
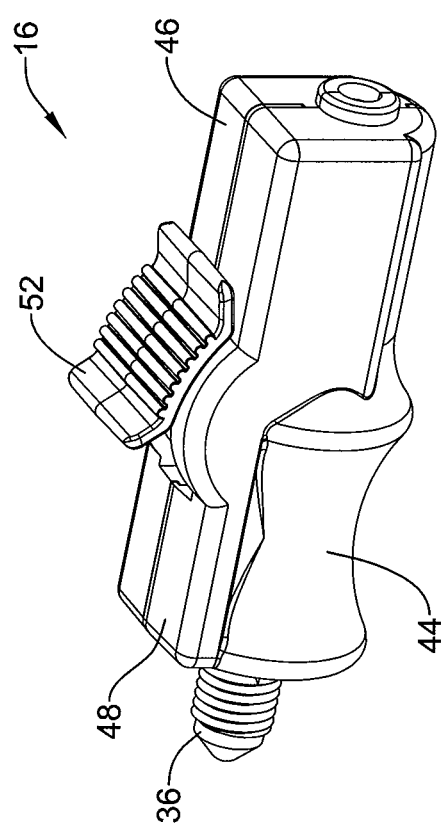
FIG. 3 is a perspective view of the handle assembly of the drainage catheter delivery system of FIG. 1.
Figure 4:
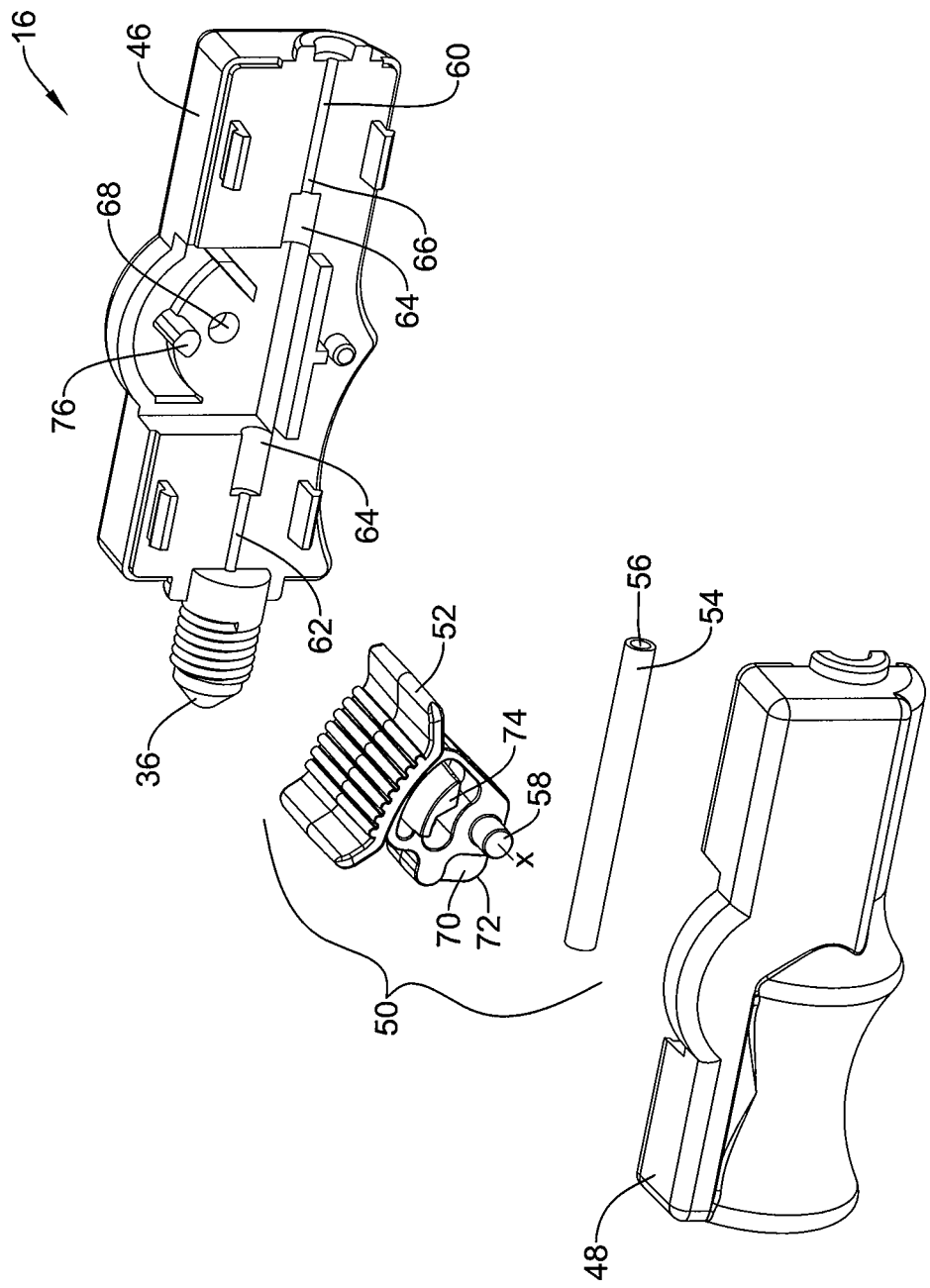
FIG. 4 is an exploded view of the handle assembly of FIG. 3.

The handle assembly 16, further illustrated in FIGS. 3 and 4, may include a housing 44. The housing 44, in some embodiments, may be formed as a unitary component or of a multiple component construction. For instance, as shown in FIG. 4, the housing 44 may include a first portion 46 coupled to a second portion 48. The housing 44, or components thereof, may be molded, cast, milled or otherwise formed from a desired material, such as a polymeric material. The housing 44 may include a bore 60 extending through the housing 44 from the proximal end to the distal end of the housing 44. The bore 60 may include a first cylindrical portion 62 having a first diameter, a second cylindrical portion 64 having a second diameter, and a third cylindrical portion 66 having a third diameter. The diameter of the first and third portions 62, 66 may be substantially equal, and the diameter of the second portion 64, located between the first and third portions 62, 66 may be larger than the diameter of the first and third portions 62, 66. The first portion 46 of the housing 44 may be formed to define a first half of the bore 60, and the second portion 48 of the housing 44 may be formed to define a second half (not shown) of the bore 60. When assembled, the portions 46, 48 of the housing 44 may collectively define the bore 60.

The handle assembly 16 may further include a locking mechanism 50 which may be actuatable to selectively lock the elongate member 40 from longitudinal movement relative to the handle assembly 16 and the push catheter 14. The locking mechanism 50 may include an actuator 52, such as a lever, knob, button, toggle, switch or other control mechanism which may be manipulated by an operator during a medical procedure to selectively lock the guide catheter 12 from longitudinal movement relative to the push catheter 14 and handle assembly 16.

The actuator 52 may be actuatably attached to the housing 44 of the handle assembly 16. For instance, as shown in FIGS. 3 and 4, the actuator 52 may be pivotably attached to the housing 44 about a pivot axis X. The actuator 52, and thus the locking mechanism 50, may be actuatable between a first position and a second position as will be discussed in more detail herein.

The locking mechanism 50 may further include a flexible member, such as a flexible tubular member 54 disposed in the second portion 64, or enlarged portion, of the bore 60 extending through the housing 44 of the handle assembly 16. The flexible tubular member 54 may be concentric with the bore 60, such that the flexible tubular member 54 has a central longitudinal axis which is collinear with the central longitudinal axis of the bore 60. In some embodiments, the flexible tubular member 54 may have a central lumen 56 extending through the flexible tubular member 54 which is sized to receive the elongate member 40. For instance, the lumen 56 of the flexible tubular member 54 may have a diameter substantially equal to the diameter of the first and/or third portions 62, 66 of the bore 60. In some embodiments, the flexible member may be a portion of a tube or another geometric piece of flexible material. In some instances, the flexible member may be integral with the actuator 52 of the locking mechanism 50. In some instances, the flexible member may be a polymeric material, such as a thermoplastic elastomer, molded into the actuator 52.

The flexible tubular member 54 may be formed of any desired material giving the flexible tubular member 54 a desired amount of flexibility and/or compressibility. For instance, the flexible tubular member 54 may be formed of silicone or other flexible polymeric material. Silicone may be desirable for its rubber-like properties and its ability to frictionally grip the elongate member 40 extending through the flexible tubular member 54 when compressed against the elongate member 40 of the guide catheter 12. In some instances, the flexible tubular member 54 may be coated with a material having a high coefficient of friction to enhance the frictional engagement with the elongate member 40.

The handle assembly 16 may be assembled such that the flexible tubular member 54 is disposed in the bore 60 and the actuator 52 is pivotably coupled with a pin 58 to the housing 44. The pin 58 may be an integral portion of the housing 44 or the actuator 52, or the pin 58 may be a separate component coupled between the housing 44 and the actuator 52. As shown in FIG. 4, the pin 58 may be an integral portion of the actuator 52 inserted into and/or through a bore 68 of the housing 44.

Figure 5:
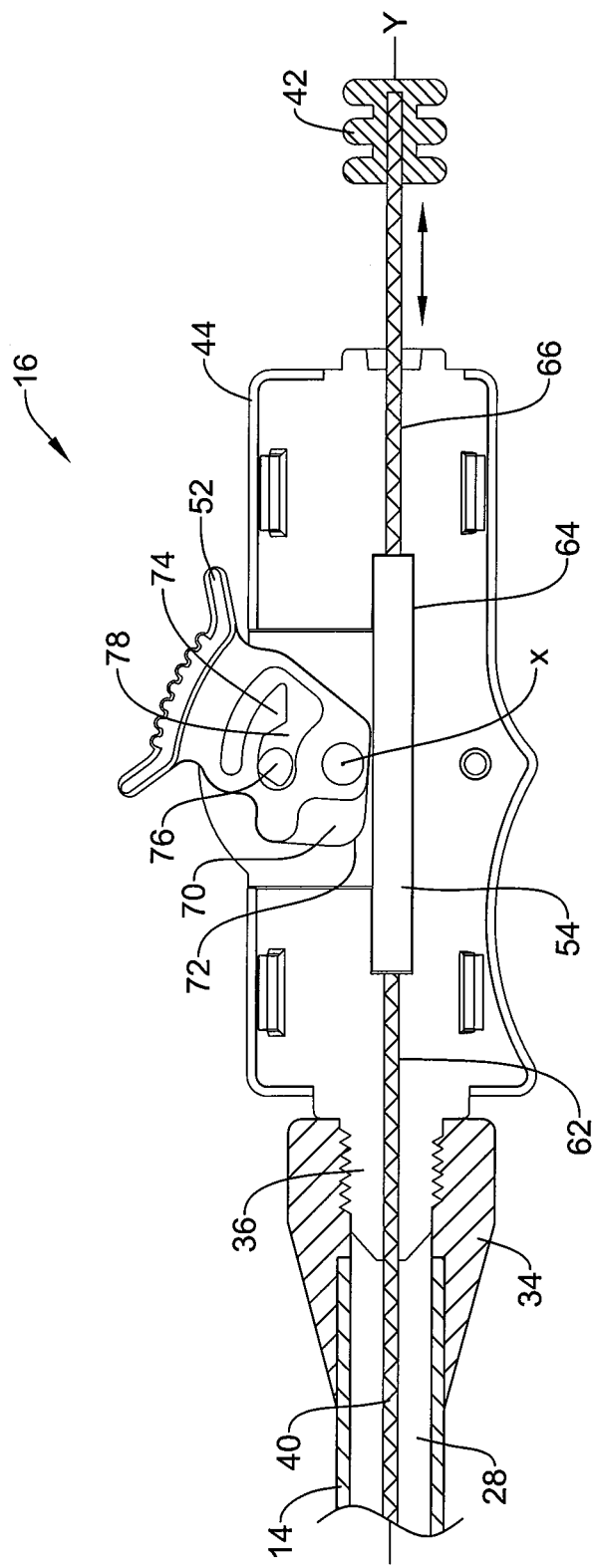
FIGS. 5 and 6 are cross-sectional views of the handle assembly of FIG. 3 illustrating unlocked and locked positions of the locking mechanism of the handle assembly.
Figure 6:
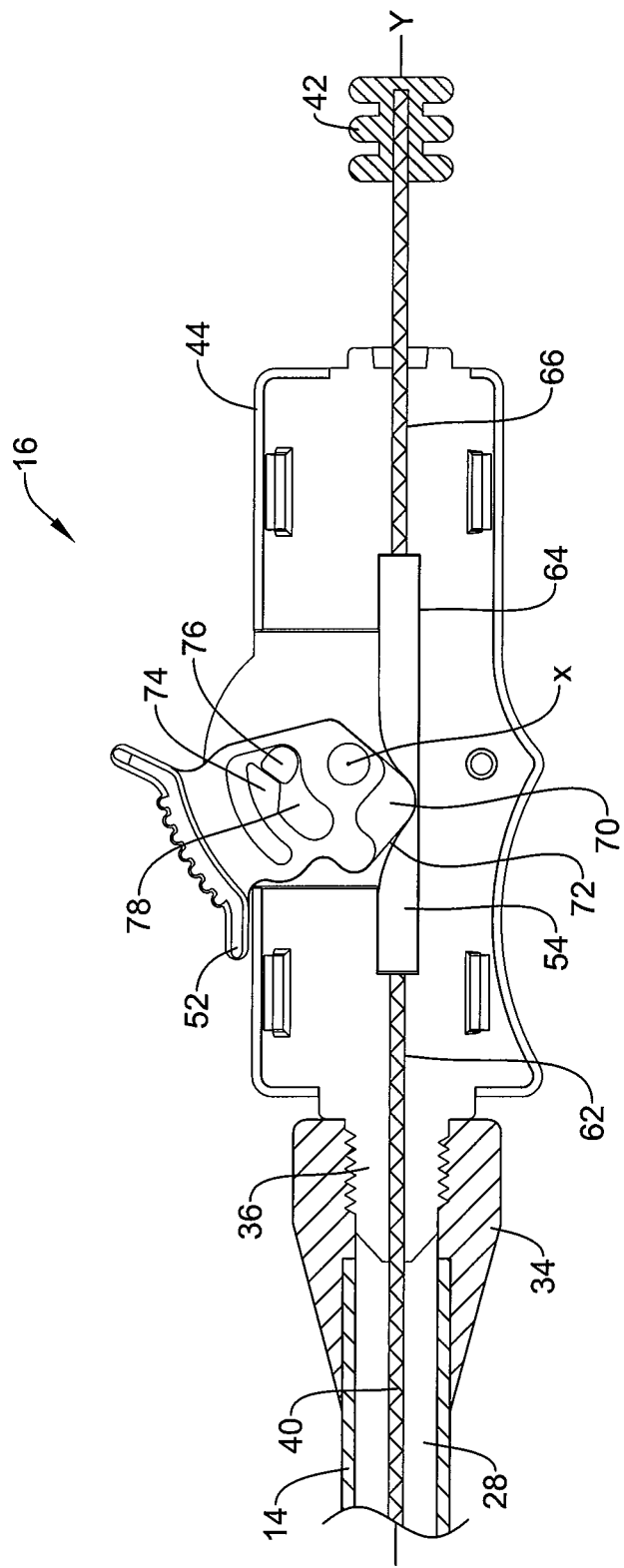

Actuation of the locking mechanism 50 of the handle assembly 16 will be further discussed while referring to FIGS. 5 and 6. FIG. 5 illustrates the locking mechanism 50 in a first position in which the elongate member 40 is free to move longitudinally through the handle assembly 16 as shown by the arrow. FIG. 6 illustrates the locking mechanism 50 in a second position in which the elongate member 40 is locked from movement in a longitudinal direction relative to the handle assembly 16. When saying that the elongate member 40 is locked from longitudinal movement, it is intended to mean that the elongate member 40 is restrained from longitudinal movement through the handle assembly 16 under ordinary operational conditions. Thus, it is understood that in the second, or locked position, the force required to longitudinally move the elongate member 40 through the handle assembly 16 is notably greater than the force required to longitudinal move the elongate member 40 through the handle assembly 16 in the first, unlocked position. In some instances, the locking mechanism 50 may be positionable at additional positions, imposing varying levels of friction or locking to elongate member 40. For example, the locking mechanism 50 may include one or more intermediate positions between the first, unlocked position and the second, locked position which provide varying degrees of frictional engagement of the elongate member 40.

As shown in FIG. 5, the flexible tubular member 54 may be disposed in the second portion 64 of the bore 60 of the housing 44. The elongate member 40 may extend through the bore 60 and the lumen 56 of the flexible tubular member 54. In the unlocked position, the actuator 52 does not appreciably compress the flexible tubular member 54 against the elongate member 40. In some embodiments, the actuator 52 may not contact the flexible tubular member 54 in the unlocked position shown in FIG. 5 or may contact the flexible tubular member 54 only slightly, thus not appreciably compressing or deforming the flexible tubular member 54.

As shown in FIG. 6, when the actuator 52 is actuated to the locked position, the actuator 52 compresses or deforms the flexible tubular member 54 against the elongate member 40. The frictional engagement between the flexible tubular member 54 in the deformed or compressed state restricts and/or locks the elongate member 40 from longitudinal movement relative to the handle assembly 16.

Thus, in the first, unlocked position shown in FIG. 5 there may be a first coefficient of friction between the inner surface of the flexible tubular member 54 and the outer surface of the elongate member 40, and in the second, locked position shown in FIG. 6 there may be a second coefficient of friction between the inner surface of the flexible tubular member 54 and the outer surface of the elongate member 40 which is greater than the first coefficient of friction. The increase in the coefficient of friction between the flexible tubular member 54 and the elongate member 40 may be attributed to the increased normal force applied to the elongate member 40 from the flexible tubular member 54 through actuation of the actuator 52 of the locking mechanism 50.

The actuator 52, which may be a cam member, may include an eccentric or cam portion 70 having an eccentric or cam surface 72 configured to contact the outer surface of the flexible tubular member 54. The eccentric or cam surface 72 has a variable distance from the pivot axis X such that in the first position, the eccentric or cam surface 72 is located a first distance from the longitudinal axis Y of the elongate member 40, and in the second position, the eccentric or cam surface 72 is located a second distance from the longitudinal axis Y of the elongate member 40. As shown in FIGS. 5 and 6, as the eccentric or cam surface 72 moves closer to the longitudinal axis Y of the elongate member 40, a greater compressive force is exerted on the flexible tubular member 54 to compress and/or deform the flexible tubular member 54 against the elongate member 40. In some instances, the cam surface 72 may be enhanced through roughening or with small teeth, bumps or grooves to further grip the flexible tubular member 54. Similarly, the elongate member 40 and/or the inside or outside of the flexible tubular member 54 could be coated, roughened or include small teeth, bumps or grooves to enhance engagement between the components.

The locking mechanism 50 may additionally include a detent which restricts pivotable movement of the actuator 52 to the first, unlocked position from the second, locked position. In some instances the detent may be an over-center locking mechanism or a deflectable mechanism. For instance, as shown in FIGS. 5 and 6, the actuator 52 may include a tang 74, and the housing 44 may include a projection 76. The projection 76 of the housing 44 may extend into an arcuate opening 78 of the actuator 52. As the actuator 52 is moved to the second, locked position, the tang 74 is deflected as the tang 74 rides against the projection 76 until the end of the tang 74 passes the projection 76, at which point the end of the tang 74 may engage against the projection 76. In order to move the actuator 52 back to the first position, the operator must overcome the additional force necessary to disengage the tang 74 from the projection 76 by deflecting the tang 74. In some embodiments, the locking mechanism 50 may include an actuatable trigger or lock release mechanism which could be actuated or activated by a user prior to pivoting or otherwise actuating the actuator 52.

During a medical procedure, the locking mechanism 50 of the handle assembly 16 may be positioned in the locked position during advancement of the drainage catheter 20, positioned on the guide catheter 12 of the drainage catheter delivery system 10, as the drainage catheter delivery system 10 is advanced to a target location in a body lumen. Once the drainage catheter 20 has been advanced to the target location, the locking mechanism 50 may be actuated to the unlocked position (e.g., the actuator 52 may be actuated from the second position to the first position) to allow the elongate member 40 of the guide catheter 12 to move longitudinally relative to the push catheter 14 and the handle assembly 16. The operator may then withdraw the guide catheter 12 proximally relative to the push catheter 14 and the handle assembly 16. For instance, the operator may grasp the knob 42 with one hand and the handle assembly 16 with another hand, then pull the knob 42 proximally away from the handle assembly 16 to withdraw the guide catheter 12. Withdrawing the guide catheter 12 proximally relative to the push catheter 14 and the handle assembly 16 may release the drainage catheter from the guide catheter 12 and push catheter 14 in order to deploy the drainage catheter 20 at the target location. For instance, if a releasing means is utilized which releasably connects the push catheter 14 to the drainage catheter 20 as disclosed in U.S. Pat. Nos. 5,921,952 and 6,562,024, the disclosures of which are incorporated herein by reference, proximal longitudinal movement of the guide catheter 12 such that the distal end of the guide catheter 12 is proximal of the distal end of the push catheter 14 will release the drainage catheter 20 from the push catheter 14 for deployment in the lumen.

Thus, it can be seen that the locking mechanism 50 may prevent relative longitudinal movement of the guide catheter 12 relative to the push catheter 14 and the handle assembly 16 until it is desired to release the drainage catheter 20 from the push catheter 14. Therefore, inadvertent premature deployment of the drainage catheter 20 may be avoided.

Figure 7:
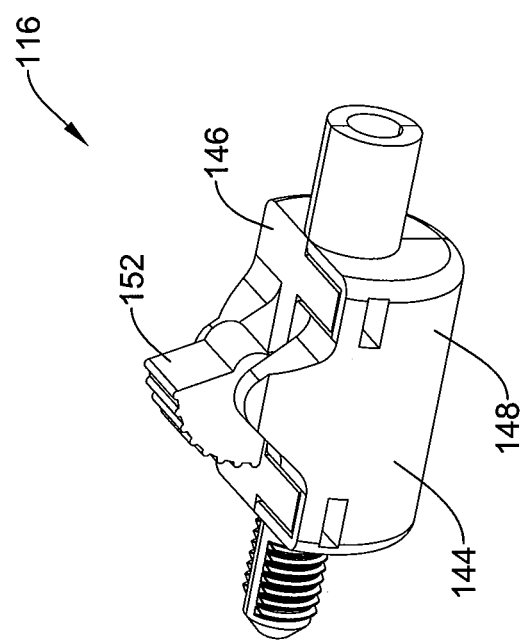
FIG. 7 is a perspective view of an alternative embodiment of a handle assembly having a locking mechanism.
Figure 8:
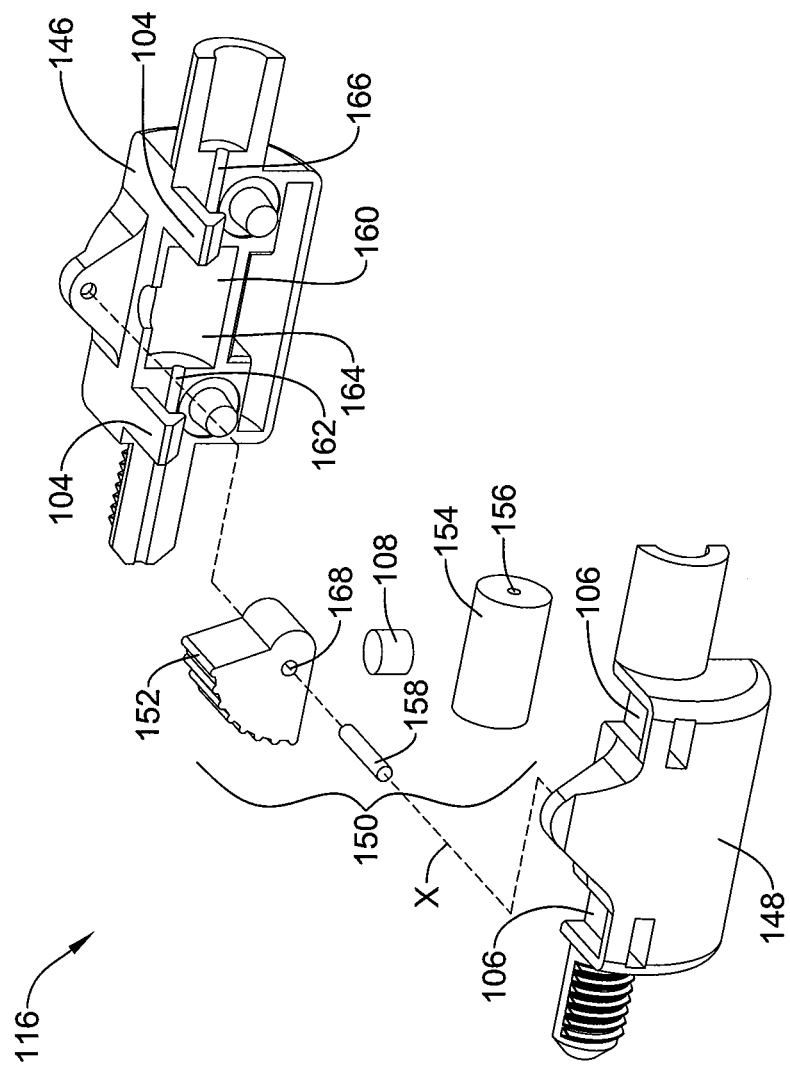
FIG. 8 is an exploded view of the handle assembly of FIG. 7.

FIGS. 7 and 8 illustrate another embodiment of a handle assembly 116, similar to the handle assembly 16, for a medical device, such as a catheter assembly. The handle assembly 116 may include a housing 144. The housing 144, in some embodiments, may be formed as a unitary component or of a multiple component construction. For instance, as shown in FIGS. 7 and 8, the housing 144 may include a first portion 146 coupled to a second portion 148. As shown in the figures, the first portion 146 may snap fit to the second portion 148 when the first and second portions 146, 148 are brought together. For instance, the first portion 146 may include one or more male interlocking components 104 which interlock with one or more female interlocking components 106 of the second portion 148.

The housing 144 may include a bore 160 extending through the housing 144 from the proximal end to the distal end of the housing 144. The bore 160 may include a first cylindrical portion 162 having a first diameter, a second cylindrical portion 164 having a second diameter, and a third cylindrical portion 166 having a third diameter. The diameter of the first and third portions 162, 166 may be substantially equal, and the diameter of the second portion 164, located between the first and third portions 162, 166 may be larger than the diameter of the first and third portions 162, 166. The first portion 146 of the housing 144 may be formed to define a first half of the bore 160 and the second portion 148 of the housing 144 may be formed to define a second half (not shown) of the bore 160. When assembled, the portions 146, 148 of the housing 144 may collectively define the bore 160.

The handle assembly 116 may further include a locking mechanism 150 which may be actuatable to selectively lock the elongate member 40 from longitudinal movement relative to the handle assembly 116 and the push catheter 14. The locking mechanism 150 may include an actuator 152, such as a lever, knob, button, toggle, switch or other control mechanism which may be manipulated by an operator during a medical procedure to selectively lock the guide catheter 12 from longitudinal movement relative to the push catheter 14 and handle assembly 116.

The actuator 152 may be actuatably attached to the housing 144 of the handle assembly 116. For instance, as shown in FIG. 8, the actuator 152 may be pivotably attached to the housing 144 about a pivot axis X. The actuator 152, and thus the locking mechanism 150, may be actuatable between a first position and a second position as will be discussed in more detail herein.

The locking mechanism 150 may also include a flexible member, such as a flexible tubular member 154 disposed in the second portion 164, or enlarged portion, of the bore 160 extending through the housing 144 of the handle assembly 116. The flexible tubular member 154 may be concentric with the bore 160, such that the flexible tubular member 154 has a central longitudinal axis which is collinear with the central longitudinal axis of the bore 160. In some embodiments, the flexible tubular member 154 may have a central lumen 156 extending through the flexible tubular member 154 which is sized to receive the elongate member 40. For instance, the lumen 156 of the flexible tubular member 154 may have a diameter substantially equal to the diameter of the first and/or third portions 162, 166 of the bore 160. In some embodiments, the flexible member may be a portion of a tube or another geometric piece of flexible material. In some instances, the flexible member may be integral with the actuator 152 of the locking mechanism 150. In some instances, the flexible member may be a polymeric material, such as a thermoplastic elastomer, molded into the actuator 152.

The flexible tubular member 154 may be formed of any desired material giving the flexible tubular member 154 a desired amount of flexibility and/or compressibility. For instance, the flexible tubular member 154 may be formed of silicone or other flexible polymeric material. Silicone may be desirable for its rubber-like properties and its ability to frictionally grip the elongate member 40 extending through the flexible tubular member 154 when compressed against the elongate member 40 of the guide catheter 12. In some instances, the flexible tubular member 154 may be coated with a material having a high coefficient of friction to enhance the frictional engagement with the elongate member 40.

The handle assembly 116 may further include a push member 108 positioned between the actuator 152 and the flexible tubular member 154. The push member 108 may be located in a bore of the housing 144 which is transverse to the bore 160. In some embodiments, the push member 108 may extend from a location exterior of the housing 144 to a location within the housing 144.

The handle assembly 16 may be assembled such that the flexible tubular member 154 is disposed in the bore 160, the actuator 152 is pivotably coupled to a pin 158 in the housing 144, and the push member 108 is disposed between the flexible tubular member 154 and the actuator 152. The pin 158 may be an integral portion of the housing 144 or actuator 152, or the pin 158 may be a separate component coupled between the housing 144 and the actuator 152. The pin 158 may be inserted into and/or through a bore 168 of the actuator 152.

Figure 9:
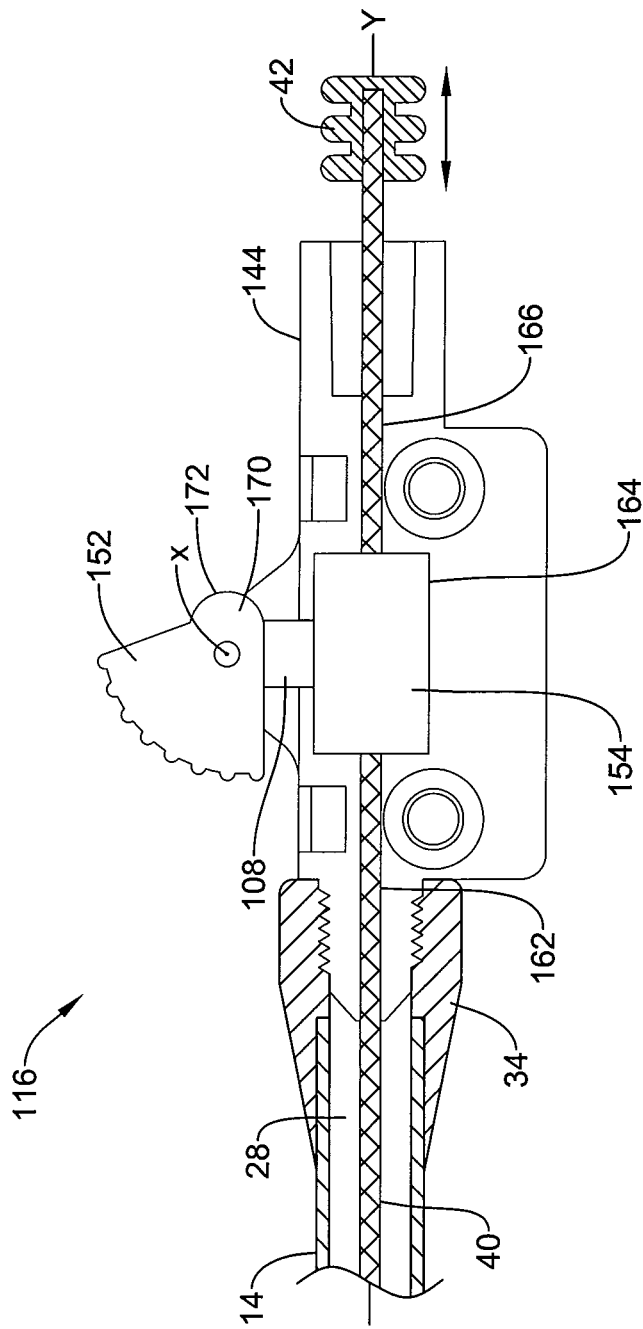
FIGS. 9 and 10 are cross-sectional views of the handle assembly of FIG. 7 illustrating unlocked and locked positions of the locking mechanism of the handle assembly.
Figure 10:
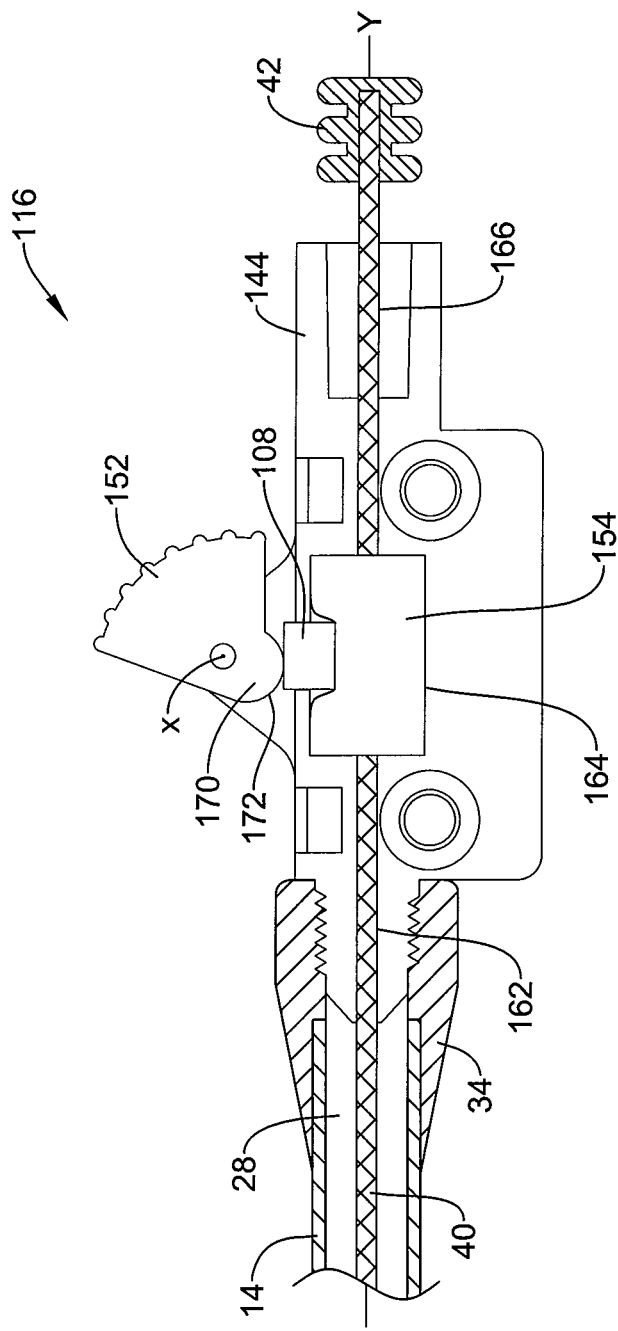

Actuation of the locking mechanism 150 of the handle assembly 116 will be further discussed while referring to FIGS. 9 and 10. FIG. 9 illustrates the locking mechanism 150 in a first position in which the elongate member 40 is free to move longitudinally through the handle assembly 116. FIG. 10 illustrates the locking mechanism 150 in a second position in which the elongate member 40 is locked from movement in a longitudinal direction relative to the handle assembly 116. When saying that the elongate member 40 is locked from longitudinal movement, it is intended to mean that the elongate member 40 is restrained from longitudinal movement through the handle assembly 116 under ordinary operational conditions. Thus, it is understood that in the second, or locked position, the force required to longitudinally move the elongate member 40 through the handle assembly 116 is greater than the force required to longitudinal move the elongate member 40 through the handle assembly 116 in the first, unlocked position. In some instances, the locking mechanism 150 may be positionable at additional positions, imposing varying levels of friction or locking to elongate member 40. For example, the locking mechanism 150 may include one or more intermediate positions between the first, unlocked position and the second, locked position which provide varying degrees of frictional engagement of the elongate member 40.

As shown in FIG. 9, the flexible tubular member 154 may be disposed in the second portion 164 of the bore 160 of the housing 144. The elongate member 40 may extend through the bore 160 and the lumen 156 of the flexible tubular member 154. In the unlocked position, the flexible tubular member 154 is not appreciably compressed against the elongate member 40. In some embodiments, the push member 108 may not contact the flexible tubular member 154 in the unlocked position shown in FIG. 9 or may contact the flexible tubular member 154 only slightly, thus not appreciably compressing or deforming the flexible tubular member 154.

As shown in FIG. 10, when the actuator 152 is actuated to the locked position, the actuator 152 forces the push member 108 toward the longitudinal axis Y of the elongate member 40, compressing or deforming the flexible tubular member 154 against the elongate member 40. The frictional engagement between the flexible tubular member 154 in the deformed or compressed state restricts and/or locks the elongate member 40 from longitudinal movement relative to the handle assembly 116.

Thus, in the first, unlocked position shown in FIG. 9 there may be a first coefficient of friction between the inner surface of the flexible tubular member 154 and the outer surface of the elongate member 40, and in the second, locked position shown in FIG. 10 there may be a second coefficient of friction between the inner surface of the flexible tubular member 154 and the outer surface of the elongate member 40 which is greater than the first coefficient of friction. The increase in the coefficient of friction between the flexible tubular member 154 and the elongate member 40 may be attributed to the increased normal force applied to the elongate member 40 from the flexible tubular member 154 through actuation of the actuator 152 of the locking mechanism 150.

The actuator 152, which may be a cam member, may include an eccentric or cam portion 170 having an eccentric or cam surface 172 configured to contact the push member 108. The eccentric or cam surface 172 has a variable distance from the pivot axis X such that in the first position the eccentric or cam surface 172 is located a first distance from the longitudinal axis Y of the elongate member 40 and in the second position the eccentric or cam surface 172 is located a second distance from the longitudinal axis Y of the elongate member 40. As shown in FIGS. 9 and 10, as the eccentric or cam surface 172 moves closer to the longitudinal axis Y of the elongate member 40, the push member 108, which rides against the eccentric or cam surface 172, is moved toward the longitudinal axis Y and against the flexible tubular member 154 such that a greater compressive force is exerted on the flexible tubular member 154 to compress and/or deform the flexible tubular member 154 against the elongate member 40. In some instances, the cam surface 172 may be enhanced through roughening or with small teeth, bumps or grooves to further grip the flexible tubular member 154. Similarly, the elongate member 40 and/or the inside or outside of the flexible tubular member 154 could be coated, roughened or include small teeth, bumps or grooves to enhance engagement between the components.

The locking mechanism 150 may additionally include a detent which restricts pivotable movement of the actuator 152 to the first, unlocked position from the second, locked position. For instance, as shown in FIGS. 9 and 10, the eccentric or cam surface 172 of the eccentric or cam portion 170 of the actuator 152 may be configured such that an intermediate portion of the eccentric or cam surface 172 is located a greater distance from the pivot axis X than portions of the eccentric or cam surface 172 on either side of the intermediate portion. Thus, as the actuator 152 is pivoted to the second position from the first position, the push member 108 moves closer to the longitudinal axis Y as the push member 108 follows the eccentric or cam surface 172 until the push member 108 moves past the intermediate portion of the eccentric or cam surface 172, at which point the push member 108 may move away from the longitudinal axis Y slightly as the push member 108 continues to follow the eccentric or cam surface 172. In order to move the actuator 152 back to the first position, the operator must overcome the additional force necessary to urge the push member 108 toward the longitudinal axis Y so that the intermediate portion of the eccentric or cam surface 172 may move past the push member 108 in the opposite direction. In other words, the shape of the eccentric or cam portion 170 may create an over-center locking mechanism for engaging against the push member 108. In some embodiments, the locking mechanism 150 may include an actuatable trigger or lock release mechanism which could be actuated or activated by a user prior to pivoting or otherwise actuating the actuator 152.

Figure 11A:
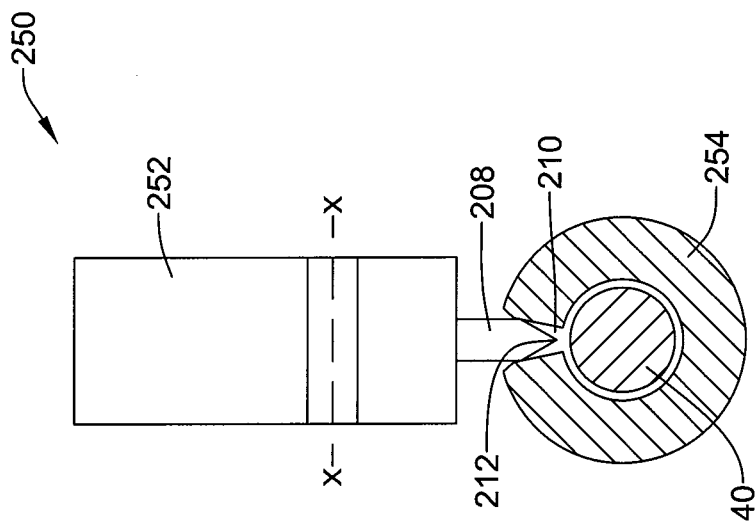
FIG. 11A is a cross-sectional view of the locking assembly of FIG. 11 taken along line 11A-11A.
Figure 11:
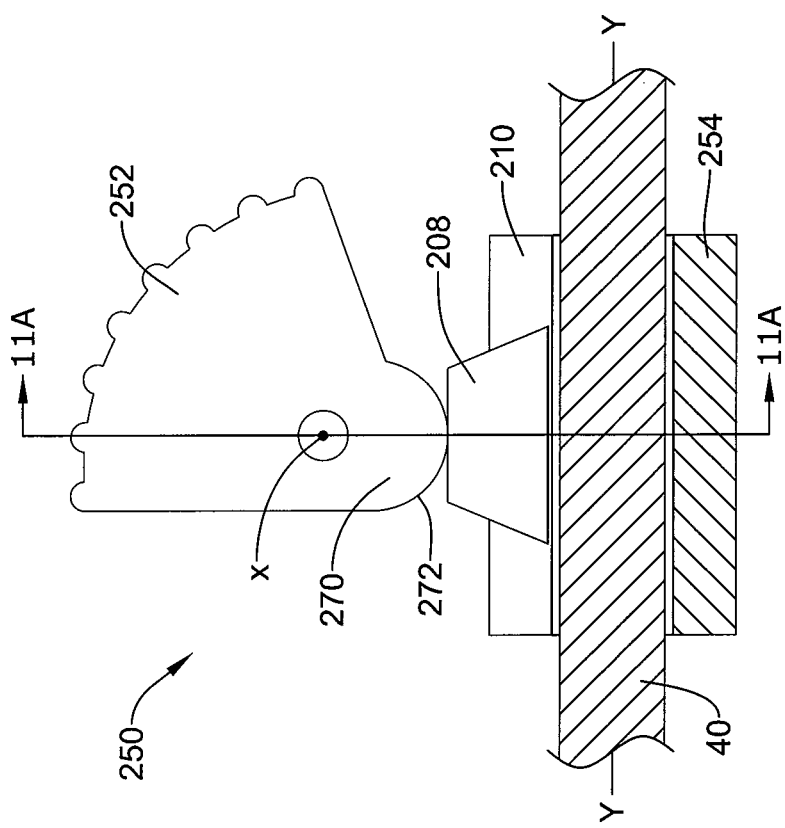
FIG. 11 is a cross-sectional view of an alternative locking assembly which may be incorporated into a handle assembly of a medical device in a first, unlocked position.

Another locking mechanism 250 which may be incorporated in a handle assembly of a medical device to selectively lock longitudinal movement of a first elongate member relative to a second elongate member is illustrated in FIGS. 11 and 12. FIGS. 11 and 11A illustrate the locking mechanism 250 in a first, unlocked position in which the elongate member 40 may longitudinally move relative to a handle assembly of a medical device. FIGS. 12 and 12A illustrate the locking mechanism 250 in a second, locked position in which the elongate member 40 is restrained or locked from longitudinal movement relative to a handle assembly of a medical device.

The locking mechanism 250 may include an actuator 252, such as a lever, knob, button, toggle, switch or other control mechanism which may be manipulated by an operator during a medical procedure to selectively lock the elongate member 40 relative to a handle assembly of a medical device. The actuator 252, which may be a cam member, may include an eccentric or cam portion 270 having an eccentric or cam surface 272 which rides against a push member 208 of the locking mechanism 250. The push member 208, which may have a pointed tip 212, may extend into a slit 210 of a tubular member 254 of the locking mechanism 250 which surrounds the elongate member 40. The tubular member 254 may be a flexible tubular member or the tubular member 254 may be rigid in some instances.

As shown in FIGS. 11 and 11A, in the unlocked position, the presence of the push member 208 in the slit 210 widens the slit 210 to a first width between opposing edges of the tubular member 254 extending through the sidewall of the tubular member 254. Widening of the slit 210 may enlarge the inner diameter of the tubular member 254 to a diameter larger than the elongate member 40, allowing the elongate member 40 to freely move longitudinally through the tubular member 254 in the unlocked position.

The actuator 252 may be actuated, for example, pivoted about the pivot axis X from a first position shown in FIG. 11 to a second position shown in FIG. 12. As the actuator 252 is pivoted, the push member 208 may move in a direction away from the longitudinal axis Y of the elongate member 40 as the push member 208 follows the eccentric or cam surface 272 of the eccentric or cam portion 270 of the actuator 252, thereby withdrawing the push member 208 from the slit 210. As the push member 208 is withdrawn from the slit 210, the tubular member 254 tends to move toward an equilibrium position, decreasing the width of the slit 210, and thus reducing the inner diameter of the tubular member 254. In an equilibrium position, the inner diameter of the tubular member 254 may be less than or equal to the diameter of the elongate member 40. Thus, as the tubular member 254 moves toward the equilibrium position, the inner surface of the tubular member 254 engages or contacts the outer surface of the elongate member 40, creating frictional contact with the elongate member 40. In the second position shown in FIGS. 12 and 12A, substantially the entire inner surface of the tubular member 254 may contact the outer surface of the elongate member 40. In some instances the elongate member 40 and/or the inner surface of the tubular member 254 could be coated, roughened or include small teeth, bumps or grooves to enhance the frictional engagement between the elongate member 40 and the tubular member 254.

In some embodiments, the presence of the elongate member 40 through the lumen of the tubular member 254 may prevent the tubular member 254 from fully returning to an equilibrium position, thus the tubular member 254 may exert a radially inward force on the elongate member 40 in the locked position shown in FIGS. 12 and 12A, generating a frictional force between the elongate member 40 and the tubular member 254 to restrain the elongate member 40 from longitudinal movement through the tubular member 254.

From the locked position shown in FIG. 12, the actuator 252 may be actuated, for example, pivoted about the pivot axis X back to the first position shown in FIG. 11. As the actuator 252 is pivoted, the push member 208 may move in a direction toward the longitudinal axis Y of the elongate member 40 as the push member 208 follows the eccentric or cam surface 272 of the eccentric or cam portion 270 of the actuator 252, thereby urging the push member 208 into the slit 210 to widen the slit 210. In this position, the elongate member 40 may again be longitudinally moveable through the lumen of the tubular member 254, and thus longitudinally moveable relative to the handle assembly of the medical device.

Thus, in the first, unlocked position shown in FIGS. 11 and 11A there may be a first coefficient of friction between the inner surface of the tubular member 254 and the outer surface of the elongate member 40, and in the second, locked position shown in FIGS. 12 and 12A there may be a second coefficient of friction between the inner surface of the tubular member 254 and the outer surface of the elongate member 40 which is greater than the first coefficient of friction. The increase in the coefficient of friction between the tubular member 254 and the elongate member 40 may be attributed to the increased normal force applied to the elongate member 40 from the tubular member 254 as the tubular member 254 compresses around the elongate member 40 as the tubular member 254 reverts toward an equilibrium condition.

In some instances, the locking mechanism 250 may be positionable at additional positions, imposing varying levels of friction or locking to elongate member 40. For example, the locking mechanism 250 may include one or more intermediate positions between the first, unlocked position and the second, locked position which provide varying degrees of frictional engagement of the elongate member 40. Furthermore, in some embodiments, the locking mechanism 250 may include an actuatable trigger or lock release mechanism which could be actuated or activated by a user prior to pivoting or otherwise actuating the actuator 252.

In some instances, the elongate member 40 may include a bend, notch, recess, or similar structure into which the actuator 52, 152, 252 extends into and engages with in the second, unlocked position. Actuation of the actuator 52, 152, 252 to the first, unlocked position may disengage the actuator 52, 152, 252 from the bend, notch, recess or similar structure of the elongate member 40 to permit longitudinal movement of the elongate member 40 relative to the handle assembly.

Although the handle assemblies including the locking mechanisms disclosed herein have been illustrated for use with a drainage catheter delivery system, it can be appreciated that the disclosed handle assemblies may be incorporated into a variety of other medical devices. For instance, the disclosed handle assemblies and locking mechanisms may be incorporated into other medical catheter assemblies which may benefit from the ability to selectively lock a first elongate member from longitudinal movement relative to a second elongate member during portions of a medical procedure. In some instances the locking mechanisms may be incorporated with a medical catheter in order to selectively lock the medical catheter, disposed over a guidewire, from longitudinal movement relative to the guidewire.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A medical device assembly comprising:
an elongate tubular member having a proximal end and a distal end;
a handle assembly coupled to the proximal end of the elongate tubular member, the handle assembly including a housing having a bore extending therethrough and a locking mechanism, the locking mechanism comprising:
a flexible member positioned in the bore of the housing; and
an actuator pivotably attached to the housing about a pivot axis, the actuator being pivotable between a first position and a second position; and
an elongate member extending along the flexible member, the elongate member selectively longitudinally movable with respect to the housing of the handle assembly;
wherein the housing of the handle assembly includes a projection extending into an arcuate opening of the actuator, the actuator further including a detent, wherein the detent is a tang of the actuator, wherein the tang of the actuator engages the projection in the second position of the actuator to restrict pivotable movement of the actuator to the first position of the actuator;
wherein in the first position of the actuator the elongate member is longitudinally movable along the flexible member and in the second position of the actuator the flexible member is deformed against the elongate member via the actuator to restrain longitudinal movement of the elongate member relative to the flexible member through increased frictional forces between the flexible member and the elongate member;
wherein the bore of the housing includes a first portion having a first diameter and a second portion having a proximal end, a distal end, and a second diameter greater than the first diameter, wherein the first portion has an end that abuts either the proximal end or distal end of the second portion and the flexible member is positioned in the second portion of the bore and extends from the proximal end to the distal end of the second portion; and
wherein the flexible member has an outer diameter greater than the first diameter of the first portion of the bore.

2. The medical device assembly of claim 1, wherein the flexible member is a tubular member having a lumen extending therethrough, and wherein the elongate member extends through the lumen of the flexible member.

3. The medical device assembly of claim 2, wherein the lumen of the flexible member has a diameter which is substantially equal to the first diameter of the first portion of the bore of the housing.

4. The medical device assembly of claim 2, wherein in the first position the lumen of the flexible member has a first diameter and wherein in the second position the lumen of the flexible member has a second diameter less than the first diameter.

5. The medical device assembly of claim 1, wherein the flexible member is deformed against the elongate member in the second position.

6. The medical device assembly of claim 1, wherein the elongate member extends along a longitudinal axis;
wherein the actuator includes an eccentric surface having a variable distance from the pivot axis; and
wherein in the first position the eccentric surface of the actuator is located a first distance from the longitudinal axis and in the second position the eccentric surface of the actuator is located a second distance from the longitudinal axis which is less than the first distance.

7. The medical device assembly of claim 6, wherein in the second position, the eccentric surface of the actuator is engaged against the flexible member, forcing the flexible member against the elongate member.

8. A medical catheter assembly comprising:
an outer tubular member having a proximal end, a distal end and a lumen extending therethrough;
an inner tubular member slidably disposed in the lumen of the outer tubular member and wherein the inner tubular member extends distally from within and beyond the outer tubular member;
a handle assembly coupled to the proximal end of the outer tubular member, the handle assembly including a housing having a proximal end and a distal end, the housing including a bore extending therethrough; and
an elongate member affixed to the inner tubular member and extending proximally therefrom through the lumen of the outer tubular member into the bore of the housing;
wherein the handle assembly includes a locking mechanism including an actuator actuatable between a first position and a second position, and a flexible member positioned in the bore of the housing, wherein the flexible member is a tubular member having a lumen extending therethrough, and wherein the elongate member extends through the lumen of the flexible member, the flexible member configured to frictionally engage the elongate member; and
wherein in the first position the elongate member and the inner tubular member are longitudinally movable relative to the outer tubular member and the handle assembly, and in the second position the actuator forces the flexible member against the elongate member to restrain longitudinal movement of the elongate member relative to the handle assembly.

9. The medical catheter assembly of claim 8, wherein in the first position there is a first coefficient of friction between a surface of the flexible member and an outer surface of the elongate member, and in the second position there is a second coefficient of friction between the surface of the flexible tubular member and the outer surface of the elongate member, the second coefficient of friction being greater than the first coefficient of friction.

10. The medical catheter assembly of claim 8, wherein the elongate member extends along a longitudinal axis;
wherein the actuator is pivotably attached to the housing about a pivot axis;
wherein the actuator includes an eccentric surface having a variable distance from the pivot axis; and
wherein in the first position the eccentric surface of the actuator is located a first distance from the longitudinal axis and in the second position the eccentric surface of the actuator is located a second distance from the longitudinal axis which is less than the first distance.

11. The medical catheter assembly of claim 10, wherein in the second position, the eccentric surface of the actuator exerts a force against the flexible member, forcing the flexible member against the elongate member.

12. A method of selectively locking an elongate member of a medical device with respect to a handle assembly of the medical device, the method comprising:

using the handle assembly including a housing having a bore extending through the housing, the bore of the housing including a first portion having a first diameter, a second portion having a second diameter greater than the first diameter, and a third portion having a third diameter smaller than the second diameter, a flexible tubular member having a lumen extending therethrough, the flexible tubular member positioned in the second portion of the bore of the housing such that a central longitudinal axis of the flexible tubular member is collinear with a central longitudinal axis of the second portion of the bore, and an actuator movably attached to the housing between a first position and a second position, wherein the second portion is positioned between the first and third portions;

positioning an elongate member through the lumen of the flexible tubular member, the elongate member longitudinally movable with respect to the housing of the handle assembly with the actuator in the first position; and deforming the flexible tubular member against the elongate member by actuating the actuator to the second position, wherein in the second position the flexible tubular member is compressed against the elongate member to restrain longitudinal movement of the elongate member with respect to the housing of the handle assembly.

13. The method of claim 12, wherein the lumen of the flexible tubular member has a diameter which is substantially equal to the first diameter of the first portion of the bore of the housing.

14. The method of claim 13, wherein the actuator includes an eccentric portion which exerts a force against the flexible tubular member in the second position to compress the flexible tubular member against the elongate member.

* * * * *